United States Patent [19]

Payne et al.

[11] Patent Number: 4,990,332
[45] Date of Patent: Feb. 5, 1991

[54] NOVEL LEPIDOPTERAN-ACTIVE BACILLUS THURINGIENSIS ISOLATE

[75] Inventors: Jewel Payne; George G. Soares; Henry W. Talbot; Theresa C. Olson, all of San Diego, Calif.

[73] Assignee: Mycogen Corporation, San Diego, Calif.

[21] Appl. No.: 262,401

[22] Filed: Oct. 25, 1988

[51] Int. Cl.$^5$ .................. A61K 39/07; A01N 63/00; A01N 65/00
[52] U.S. Cl. .................. 424/93; 435/252.5; 424/84
[58] Field of Search ............ 424/93, 84; 435/252.5

[56] References Cited

U.S. PATENT DOCUMENTS

| | | | |
|---|---|---|---|
| 3,937,813 | 2/1976 | Clark, Jr. | 424/93 |
| 4,000,258 | 12/1976 | Shieh et al. | 424/93 |
| 4,277,564 | 7/1981 | Johnson | 435/252.5 |
| 4,764,372 | 8/1988 | Herrnstadt et al. | 424/93 |
| 4,910,016 | 3/1990 | Gaertner | 424/93 |

FOREIGN PATENT DOCUMENTS 303379A 3/1987 European Pat. Off. ............ 424/93

OTHER PUBLICATIONS

Terry L. Couch (1980), "mosquito Pathogenicity of *Bacillus thuringiensis* var. israelensis", Developments in Industrial Microbiology 22: 61-67.

Clayton C. Beegle (1978), "Use of Entomogenous Bacteria in Agroecosystems", Developments in Industrial Microbiology 20: 97-104.

*Primary Examiner*—Howard E. Schain
*Assistant Examiner*—Choon P. Koh
*Attorney, Agent, or Firm*—Saliwanchik & Saliwanchik

[57] ABSTRACT

The subject invention concerns a novel and useful insecticide with activity against insect pests of the order Lepidoptera. Pests in the order Lepidoptera do heavy damage to crops, e.g., cabbage and broccoli. The insecticide of the subject invention is a novel *B. thuringiensis* microbe referred to as *B.t.* PS85A1, or mutants thereof. Specifically disclosed is an asporogenous mutant designated *B.t.* PS85A1-168. The spores or crystals of *B.t.* PS85A1, or the crystals of *B.t.* PS85A1-168, are useful to control lepidopteran pests in various environments.

26 Claims, 1 Drawing Sheet a. B.t. HD-1 uncut
b. B.t. HD-1 cut with HindIII
c. B.t. PS85A1 uncut
d. B.t. PS85A1 cut with HindIII

NOVEL LEPIDOPTERAN-ACTIVE BACILLUS THURINGIENSIS ISOLATE

BACKGROUND OF THE INVENTION (1) Microbial Pesticides

*Bacillus thuringiensis* (*B.t.*) produces an insect toxin designated as δ-endotoxin. It is synthesized by the *B.t.* sporulating cell. The toxin, upon being ingested in its crystalline form by susceptible insect larvae, is transformed into biologically active moieties by the insect gut juice proteases. The primary target is insect cells of the gut epithelium, which are rapidly destroyed.

The reported activity spectrum of *B.t.* covers insect species within the order Lepidoptera, many of which are major pests in agriculture and forestry. The activity spectrum also includes the insect order Diptera, which includes mosquitos and black flies. See Couch, T. L. (1980) "Mosquito Pathogenicity of *Bacillus thuringiensis* var. *israelensis*," Developments in Industrial Microbiology 22:61-76; Beegle, C. C., (1978) "Use of Entomogenous Bacteria in Agroecosystems," Developments in Industrial Microbiology 20:97-104. *B.t.* isolates also have been shown to be active against beetles in the order coleoptera.

(2) Lepidopteran Pests

The diamondback moth *Plutella xylostella* (DBM) is a lepidopteran pest on cruciferous plants. The small larvae are foliar feeders that chew holes in the leaves. This can result in severe damage when populations are high. In addition to all the cruciferous vegetable crops, such as cabbage, broccoli, bok-choy, and cauliflower, DBM also attacks certain ornamental and greenhouse plants such as stocks, sweet alyssum, wallflower, and candytuft.

DBM is widely distributed and is found virtually wherever its host plants are grown. In the United States, Central America, Europe, and Asia, it is a major pest of crucifers. In many of these areas, it has become the most important pest, since it has developed resistance to chemical insecticides and cannot be effectively controlled. In these areas there is a desperate need for alternative control strategies. *Bacillus thuringiensis* has been somewhat effective in the past, but newer and more potent strains tailored to this species could substantially improve efficacy and fill an important need in managing this species.

BRIEF SUMMARY OF THE INVENTION

The subject invention concerns novel *Bacillus thuringiensis* (*B.t.*) isolates which have activity against all lepidopteran pests tested. For example, the novel *B.t.* isolate, known herein as *Bacillus thuringiensis* PS85A1 (*B.t.* PS85A1), has thus far been shown to be highly active against the diamondback moth.

The subject invention also includes mutants of *B.t.* PS85A1 which have pesticidal properties. For example, an asporogenous mutant of *B.t.* PS85A1 was obtained through ethylmethane sulfonate (EMS) mutagenesis. This mutant is referred to herein as *B.t.* PS85A1-168. Procedures for making other mutants of either *B.t.* PS85A1 or *B.t.* PS85A1-168 are well known in the microbiological art. Ultraviolet light and nitrosoguanidine are used extensively toward this end.

Further, the invention also includes the treatment of substantially intact *B.t.* PS85A1 cells, or mutants thereof, to prolong the pesticidal activity when the substantially intact cells are applied to the environment of a target pest. Such treatment can be by chemical or physical means, or a combination of chemical or physical means, so long as the technique does not deleteriously affect the properties of the pesticide, nor diminish the cellular capability in protecting the pesticide. The treated PS85A1 cell acts as a protective coating for the pesticidal toxin. The toxin becomes available to act as such upon ingestion by a target insect.

DETAILED DISCLOSURE OF THE INVENTION

The novel *Bacillus thuringiensis* isolate of the subject invention has the following characteristics:

Characteristics of *B.t.* PS85A1

Colony morphology—Large colony, dull surface, typical *B.t.*

Vegetative cell morphology—typical *B.t.*

Flagellar serotype—3a3b, kurstaki.

Intracellular inclusions—sporulating cells produce a bipyramidal crystal which partially encloses a smaller cuboidal crystal.

Plasmid preparations—agarose gel electrophoresis of plasmid preparations distinguishes *B.t.* PS85A1 from *B.t.* HD-1 and other *B.t.* isolates.

Alkali-soluble proteins—*B.t.* PS85A1 has a 130,000 dalton protein and a 60,000 dalton protein.

Activity—*B.t.* PS85A1 kills all Lepidoptera tested, and is more than five times as active against Diamondback Moth as *B.t.* HD-1.

*Plutella xylostella* bioassay results; *B.t.* PS85A1 LC50=0.026 ug/ml *B.t.* HD-1 LC50=0.161 ug/ml

Figure 1:
FIG. 1: A Photograph of Plasmid Preparations from *B.t.* HD-1 and *B.t.* PS85A1

The cultures disclosed in this application have been deposited in the Agricultural Research Service Patent Culture Collection (NRRL), Northern Regional Research Center, 1815 North University Street, Peoria, Ill. 61604, U.S.A.

| Culture | Repository No. | Deposit date |
|---|---|---|
| *Bacillus thuringiensis* PS85A1 | NRRL B-18426 | Oct. 11, 1988 |
| *Bacillus thuringiensis* PS85A1-168 | NRRL B-18427 | Oct. 18, 1988 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture(s). The depositor acknowledges the duty to replace the deposits should the depository be unable to furnish a sample when requested, due to the condition of a deposit. All restrictions on the availability to the public of the subject culture deposits will be irrevocably removed upon the granting of a patent disclosing them.

B.t. PS85A1, NRRL B-18426, and B.t. PS85A1-168, NRRL B-18427, can be cultured using standard art media and fermentation techniques. Upon completion of the fermentation cycle, the bacteria can be harvested by first separating the B.t. spores and/or crystals from the fermentation broth by means well known in the art. The recovered B.t. spores and/or crystals can be formulated into a wettable powder, liquid concentrate, granules, or other formulations by the addition of surfactants, dispersants, inert carriers and other components to facilitate handling and application for particular target pests. These formulation and application procedures are all well known in the art.

Formulated products can be sprayed or applied onto foliage to control phytophagous beetles or caterpillars. Another approach that can be taken is to incorporate the spores and/or crystals of B.t. PS85A1 or B.t. PS85A1-168 into bait granules containing an attractant and applying these granules to the soil for control of soil-inhabiting Lepidoptera. Formulated B.t. PS85A1 or its mutants can also be applied as a seed-coating or root treatment or total plant treatment.

The B.t. PS85A1 or B.t. PS85A1-168 cells, or mutants thereof, can be treated prior to formulation to prolong the pesticidal activity when the cells are applied to the environment of a target pest. Such treatment can be by chemical or physical means, or by a combination of chemical and/or physical means, so long as the technique does not deleteriously affect the properties of the pesticide, nor diminish the cellular capability in protecting the pesticide. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride; alcohols, such as isopropyl and ethanol; various histologic fixatives, such as Bouin's fixative and Helly's fixative (See: Humason, Gretchen. L., Animal Tissue Techniques, W. H. Freeman and Company, 1967); or a combination of physical (heat) and chemical agents that prolong the activity of the toxin produced in the cell when the cell is applied to the environment of the target pest(s). Examples of physical means are short wavelength radiation such as gamma-radiation and X-radiation, freezing, UV irradiation, lyophilization, and the like.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. PS85A1, NRRL B-18426 or B.t. PS85A1-168, NRRL B-18427

A subculture of B.t. PS85A1, NRRL B-18426 or B.t. PS85A1-168, NRRL B-18427 can be used to inoculate the following medium, a peptone, glucose, salts medium.

| Bacto Peptone | 7.5 g/l |
|---|---|
| Glucose | 1.0 g/l |
| $KH_2PO_4$ | 3.5 g/l |
| $K_2HOP_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

EXAMPLE 2

Testing of B.t. PS85A1, NRRL B-18426 Spores and Crystals

B.t. PS85A1, NRRL B-18426 spores and crystals were tested against the diamondback moth (DBM). B.t. PS85A1 has an $LC_{50}$ of 0.026 µg protein/ml in the DBM assay. The assay was conducted as follows:

Plutella xylostella Bioassay: dilutions are prepared of a spore and crystal pellet, mixed with USDA Insect Diet (Technical Bulletin 1528, U.S. Department of Agriculture), and poured into small plastic trays. Molting second instar larvae are placed on the diet mixture and held at 25° C. Mortality is recorded after four days.

EXAMPLE 3

Mutagenesis of Bacillus thuringiensis PS85A1 to Obtain B. thuringiensis PS85A1-168 Mutant An asporogenous mutant of the wild type Bacillus thuringiensis PS85A1 was obtained through ethylmethane sulfonate (EMS) mutagenesis. The procedure used was a modification of that described by Wakisaka (Wakisaka, Y. [1982] "Asporogenous Bacillus thuringiensis Mutant Producing High Yields of δ-Endotoxin," Appl. and Environmental Microbiology 1498–1500). Procedure is as follows:

1. The wild type B. thuringiensis PS85A1 was streaked out onto nutrient agar directly from a frozen vial.
2. The plates were then incubated at 30° C. for 72 hours.
3. The spores were harvested with sterile 0.05M PO4 buffer, pH 7.0.
4. The suspension was then separated into five 10 ml aliquots and a plate count was done to determine the number of spores that would be mutated.
5. The five samples were then exposed to a 70° C. water bath for 15 minutes to kill any vegetative cells present.

6. It was to these treated samples that the EMS (obtained from Sigma Chemical Company) was added. A range of doses were used.
7. After addition of the EMS, the samples were incubated for 18 hours at 30° C. and 350 rpm.
8. The treated cultures were then washed twice with sterile distilled water (centrifuge 8,000 rpm for 5 minutes).
9. The final pellets were then resuspended in sterile distilled water and 40% glycerol for storage at −70° C.

After the mutagenesis was completed, the mutated cells were plated onto nutrient agar. After a 48 hour incubation period, the colonies were randomly selected and examined microscopically for the desired phenotype. If a spo−cry+ mutant was found, it was subcultured onto nutrient agar and incubated for 48 hours to confirm that indeed it was spo−cry+. Once this had been confirmed, the culture was prepared for storage and designated by a number in the order in which it was found. These strains were then put through a primary screening in production medium. If found to be productive (in terms of toxin production) and asporogenous, further tests were pursued. These tests were developed based on criteria imposed to isolate the best spore minus mutant. The criteria are as follows: asporogenous; toxin production equal to or higher than the wild type; specific activity equal to or higher than the wild type; low reversion frequency; no beta-exotoxin production; lysis minus. To data, *B. thuringiensis* PS85A1-168 has maintained the spo−cry+ phenotype, has consistently produced equal or higher amounts of toxin than the wild type *B. thuringiensis* PS85A1, has maintained a specific activity equal to the wild type *B. thuringiensis* PS85A1, has a reversion frequency of 10e-11, has been found to be beta-exotoxin negative and lysis minus in production media.

We claim:

1. A process for controlling lepidopteran insect pests which comprises contacting said insect pests with an insect-controlling effective amount of *B. thuringiensis* PS85A1 having the identifying characteristics of NRRL B-18426, or mutants thereof.

2. The process, according to claim 1, wherein said insect pests belong to the order Lepidoptera.

3. The process, according to claim 2, wherein said insect pest is the diamondback moth.

4. The process, according to claim 1, wherein said insect pest is contacted with an insect-controlling effective amount of *B. thuringiensis* PS85A1, or mutants thereof, by incorporating said *B. thuringiensis* PS85A1 into a bait granule and placing said granule on or in the soil when planting seed of a plant upon which plant said insect pest is known to feed.

5. A process for controlling soil-inhabiting insect pests of the order Lepidoptera which comprises
   (1) preparing a bait granule comprising *B. thuringiensis* PS85A1, or mutants thereof, spores or crystals; and
   (2) placing said bait granule on or in the soil.

6. The process, according to claim 5, wherein said bait granule is applied at the same time corn seed is planted in the soil.

7. The process, according to claims 1 or 5, wherein substantially intact *B.t.* PS85A1 cells, or mutants thereof, are treated to prolong the pesticidal activity when the substantially intact cells are applied to the environment of a target pest.

8. A composition of matter comprising *B. thuringiensis* PS85A1, or mutants thereof, spores or crystals in association with an insecticide carrier.

9. The composition of matter, according to claim 8, wherein said carrier comprises beetle phagostimulants or attractants.

10. A composition of matter comprising *B. thuringiensis* PS85A1, or mutants thereof, in association with formulation ingredients applied as a seed coating.

11. *Bacillus thuringiensis* PS85A1, having the identifying characteristics of NRRL B-18426, or mutants thereof, having activity against insect pests of the order Lepidoptera.

12. A process, according to claim 1, wherein the lepidopteran pests are present on stored products.

13. A toxin(s) active against lepidopteran pests, said toxin(s) produced by *B. thuringiensis* PS85A1, having the identifying characteristics of NRRL B-18426.

14. The process, according to claim 1, wherein said mutant is an asporogenous mutant.

15. The process, according to claim 14, wherein said asporogenous mutant is designated *B.t.* PS85A1-168.

16. The process, according to claim 5, wherein said mutant is an asporogenous mutant.

17. The process, according to claim 16, wherein said asporogenous mutant is designated *B.t.* PS85A1-168.

18. The process, according to claim 7, wherein said mutant is an asporogenous mutant.

19. The process, according to claim 18, wherein said asporogenous mutant is designated *B.t.* PS85A1-168.

20. A composition of matter comprising an asporogenous mutant of *Bacillus thuringiensis* PS85A1, or mutants thereof, or crystals, in association with an insecticide carrier.

21. The composition of matter, according to claim 20, wherein said asporogenous mutant is designated *Bacillus thuringiensis* PS85A1-168, or mutants thereof, spores and/or crystals in association with an insecticide carrier.

22. The composition of matter, according to claim 21, wherein said carrier comprises beetle phagostimulants or attractants.

23. The composition, according to claim 10, wherein said mutant is an asporogenous mutant.

24. The composition, according to claim 23, wherein said asporogenous mutant is designated *B.t.* PS85A1-168.

25. Asporogenous mutant of *Bacillus thuringiensis* PS85A1, or mutants thereof.

26. *Bacillus thuringiensis* PS85A1-168, an asporogenous mutant of *Bacillus thuringiensis* PS85A1, according to claim 25.

* * * * *

UNITED STATES PATENT AND TRADEMARK OFFICE
CERTIFICATE OF CORRECTION

PATENT NO. : 4,990,332

DATED : February 5, 1991

INVENTOR(S) : Jewel M. Payne, George G. Soares, Henry W. Talbot and Theresa C. Olsen It is certified that error appears in the above-identified patent and that said Letters Patent is hereby corrected as shown below:

Column 4    line 6:    "3.5 g/l" should read --3.4 g/l--.

Signed and Sealed this

Thirteenth Day of October, 1992

Attest:

DOUGLAS B. COMER

*Attesting Officer*   *Acting Commissioner of Patents and Trademarks*